United States Patent [19]

Read et al.

[11] Patent Number: 5,795,773

[45] Date of Patent: Aug. 18, 1998

[54] DEVICE FOR DETECTING MICROORGANISMS

[75] Inventors: Karen A. Read, Timberlake; David E. Trogdon, Youngsville; Thurman C. Thorpe; Christopher S. Ronsick, both of Durham; Scott R. Jeffrey, Raleigh, all of N.C.

[73] Assignee: Akzo Nobel N.V., Arnhem, Netherlands

[21] Appl. No.: 823,279

[22] Filed: Mar. 24, 1997

Related U.S. Application Data

[63] Continuation of Ser. No. 464,014, Jun. 5, 1995, abandoned, which is a continuation-in-part of Ser. No. 410,374, Mar. 24, 1995, Pat. No. 5,518,895.

[51] Int. Cl.[6] .............................. C12M 1/34; C12M 1/24
[52] U.S. Cl. .................. 45/287.5; 435/288.1; 435/297.5; 435/304.1
[58] Field of Search .................. 435/286.6, 289.4, 435/287.5, 287.9, 288.1, 288.7, 297.5, 304.1–304.3; 422/102, 82.5–82.8; 220/360, 371; 215/248, 261; 250/341.1; 356/345, 346, 39, 412, 416, 445

[56] References Cited

U.S. PATENT DOCUMENTS

| D. 323,299 | 1/1992 | Leno . |
| 4,271,973 | 6/1981 | Quagliaro et al. ............ 251/261 |
| 4,299,921 | 11/1981 | Youssef . |
| 4,579,631 | 4/1986 | Ishikawa et al. . |
| 4,839,292 | 6/1989 | Cremonese . |
| 4,863,051 | 9/1989 | Eibner et al. ............ 215/261 |
| 4,933,082 | 6/1990 | Yamada et al. ............ 95/54 |
| 5,047,347 | 9/1991 | Cline . |
| 5,069,686 | 12/1991 | Baker et al. ............ 95/47 |
| 5,089,395 | 2/1992 | Snyder et al. . |
| 5,089,413 | 2/1992 | Nelson et al. ............ 435/305.4 |
| 5,094,955 | 3/1992 | Calandra et al. . |
| 5,116,758 | 5/1992 | Verma . |
| 5,164,301 | 11/1992 | Thompson et al. . |
| 5,188,946 | 2/1993 | Ward, Jr. et al. . |
| 5,217,876 | 6/1993 | Turner et al. . |
| 5,358,872 | 10/1994 | Mussi et al. . |
| 5,374,557 | 12/1994 | Verma . |
| 5,391,496 | 2/1995 | Kayal et al. . |
| 5,409,829 | 4/1995 | Mussi et al. . |

FOREIGN PATENT DOCUMENTS

| 2269391 | 2/1994 | United Kingdom . |
| 93/15402 | 8/1993 | WIPO . |

OTHER PUBLICATIONS

Li et al. "Scanning optical sensor for the measurement of dissolved oxygen and BOD." Sensors and Actuators, vol. B 21 (1994), pp. 143–149.

*Primary Examiner*—William H. Beisner
*Attorney, Agent, or Firm*—Gregory R. Muir

[57] ABSTRACT

A method and a sealable, sterilizable vessel for detecting the presence of microorganisms in a specimen, the vessel containing a liquid culture medium and a sensor with an indicator medium therein. A gas permeable membrane with a gas impermeable removable seal thereon are provided in a wall of the vessel. If the microorganism to be detected is an anaerobic organism, then the gas impermeable seal is left in place. If the microorganism to be detected is an aerobic organism, then the gas impermeable seal is removed so as to allow the passage of oxygen into the vessel. In a preferred embodiment, the gas permeable membrane allows the passage of oxygen into the vessel while at least partly restricting the passage of carbon dioxide to outside of the vessel. Changes in the indicator medium resulting from a change in gas production ($CO_2$, $NH_2$, $H_2S$, etc.), volatile acid production or pH concentration in the medium, are detected from outside the vessel.

29 Claims, 14 Drawing Sheets

DEVICE FOR DETECTING MICROORGANISMS

CROSS-REFERENCE TO RELATED APPLICATIONS

This is a continuation of application Ser. No. 08/464,014 filed Jun. 5, 1995, now abandoned, which is a continuation-in-part of application Ser. No. 08/410,374, filed Mar. 24, 1995, now U.S. Pat. No. 5,518,895. This application is also related to U.S. Pat. No. 5,217,876, to Turner et al. (issued Jun. 8, 1993); U.S. Pat. No. 5,094,955, to Calandra et al. (issued Mar. 10, 1992); U.S. Pat. No. 5,314,855, to Thorpe et al. (issued May 24, 1994); U.S. Pat. No. 5,164,796, to DiGuiseppi et al. (issued Nov. 17, 1992); and U.S. Pat. No. 4,945,060, to Turner et al. (issued Jul. 31, 1990), all of which patents are incorporated herein by reference.

The present invention provides a method and device for detecting/monitoring changes in pH, gas production ($CO_2$, $NH_2$, $H_2S$, etc.) or volatile acid production of a specimen using a growth medium and a sealed container without entering the container after the sample is prepared and added to the container. As a further advantage, a gas permeable membrane with a gas impermeable removable seal thereon is provided in a wall of the vessel. If the microorganism to be detected is an anaerobic organism, then the gas impermeable seal is left in place. If the microorganism to be detected is an aerobic organism, then the gas impermeable seal is removed so as to allow the passage of oxygen into the vessel. In a preferred embodiment, the gas permeable membrane is constructed so as to withstand high positive or negative pressure within the vessel, and/or to allow the passage of oxygen into the vessel while at least partly restricting the passage of carbon dioxide to outside of the vessel. A sensor is provided which changes due to differences in concentrations of gas, volatile acid and/or pH within the vessel (e.g., within the medium in the vessel).

BACKGROUND OF THE INVENTION

The presence of microorganisms in clinical specimens is conventionally determined by culturing the specimens in the presence of nutrients and detecting microbial activity through changes in the specimen or in the atmosphere over the specimen after a period of time. For example, in U.S. Pat. No. 4,182,656 to Ahnell et al the sample is placed in a container with a culture medium comprising a carbon 13 labelled fermentable substrate. After sealing the container and subjecting the specimen to conditions conducive to biological activity, the ratio of carbon 13 to carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the pressure of the gas in the container. U.S. Pat. No. 4,073,691 provides a method for determining the presence of biologically active agents, including bacteria, in a sealed container containing a culture medium by measuring changes in the character of the gaseous atmosphere over the specimen after a period of time. A method for non-invasive detection of $CO_2$ changes in the gaseous atmosphere is taught by Suppman et al, as disclosed in EPO application 83108468.6, published Apr. 4, 1984. The methods and apparatus described in these and other publications all require either a radiometric method or the invasion of the sealed container to measure changes in the gaseous atmosphere after culturing or require special materials that permit infra-red light to pass.

Other known methods for measuring microbial presence in specimens, particularly blood cultures, include measuring minute changes in temperature, pH, turbidity, color, bioluminescence, and impedance. Generally, these methods determine microbial presence or growth by detecting bacterial metabolic byproducts. Microbial presence may also be assessed by subculturing and/or staining. Of these methods, only impedance, radiometry and infra-red spectrometry provide the possibility of automated processing of clinical specimens. And except for impedance and infra-red measurements, these procedures also require entering the container in order to make a measurement on the liquid specimen or the gaseous atmosphere over the specimen. In addition to the likelihood of contamination and creating the likelihood of altering the constituency of the atmosphere over the specimen each time a determination is made, these methods do not permit taking measurements continuously or repeatedly over short time intervals for an extended period of time. This is a significant disadvantage as the growth rate of organisms differs depending on the organism and the number of organisms in the original sample, such that it cannot be predicted when detectable changes in the atmosphere or fluid sample will be presented. In a related problem, when organism growth is determined by pH changes in the liquid sample, various metabolic products will affect the pH of the sample differently. For example, the production of ammonia will raise the pH while the production of $CO_2$ will lower it. Different growth rates of different organisms could result in a pH increase at one time and a decrease at another time, which would not be detected if the pH is measured at widely spaced intervals. Another source of error when detecting changes by pH measurement in whole blood samples, particularly when an indicator dye is the means for pH determination, is the likelihood that the dye appearance can be affected or obscured by the presence of blood cells. Colorimetric indicators can only be effectively used if errors induced by the nature of the specimen can be prevented from influencing the appearance of the dye.

When the biologically active agent is an aerobic organism, a system must be provided for insuring sufficient oxygen within the vessel so that biological activity can take place. One way of providing oxygen to the vessel is by adding oxygen to the atmosphere within the vessel containing the culture medium, at the time of manufacture of the vessel. Then, when a specimen is added to the vessel by the user of the vessel, oxygen will already be present within the vessel. (A problem with this method, however, is that the shelf life of such vessels containing the pre-added oxygen and culture medium, is short.)

Another method for providing oxygen to the vessel when the microorganism is an aerobic organism, is by "spiking" the vessel at the time of culturing the organism. Often, a needle or a cannula is pierced through a stopper on the vessel so as to allow a free flow of oxygen into the vessel during culturing. One problem with this method, however, is that it requires an extra step, some skill in piercing the vessel by the user, and some danger of specimen contamination or of injury to the user by the needle. Also, if the method of culturing includes shaking for better oxygenating the culture medium, care must be taken so that the liquid culture medium does not leak outside the vessel through the needle. Also, a pierced vessel would not allow for control of the passage of carbon dioxide from out of the vessel (changes in carbon dioxide within the vessel being desirable for indicating the presence of a particular microorganism).

SUMMARY OF THE INVENTION

The present invention relates to a device and method for detecting the presence of microorganisms in clinical specimens, such as blood or other body fluids, by culturing the specimens with a sterile growth medium in a transparent sterile container having a gas permeable membrane. The presence of microorganisms is determined by detecting or measuring changes in the pH of the specimen or the production of gases (e.g., $CO_2$) or volatile acids within the container using a disposable sensor affixed to the interior surface of the container. According to the invention, microorganisms can be detected in the presence of interfering materials, such as large concentrations of red blood cells, through non-invasive means.

In the present invention, a gas impermeable seal can be removed from the gas permeable membrane when the vessel is to be used for culture of aerobic organisms. Otherwise, if the seal is left in place, the vessel can be used for the culture of anaerobic organisms. The gas permeable membrane allows for the passage of oxygen into the vessel, preferably withstands high positive or negative pressures and restricts to a sufficient degree the passage of carbon dioxide to outside the vessel, and fully restricts the passage of liquid medium to outside the vessel, even during autoclaving and shaking of the vessel.

This drawing shows the overall appearance of the functional part of the instrument, the detector assembly, with (1) the vessel, (2) sensor, (3) culture medium, the (4) light source, (5) photodetector, and the associated electronics including (6) current source, (7) current to voltage converter and (8) low pass filter.

In one embodiment, each detector assembly consists of a photodiode in a countersunk hole and one or more LED's arrayed such that light falls on the surface to be viewed, but not directly onto the detector itself. The electronic circuits in this embodiment include amplifiers and filters to condition the signals from the detectors, multiplexers to select among the signals available, and constant current sources for the illuminators.

In operation, the entire device is placed on an agitator inside an incubator, which provides a suitable environment for microbial growth and excludes room light from the photodetectors.

Figure 1:
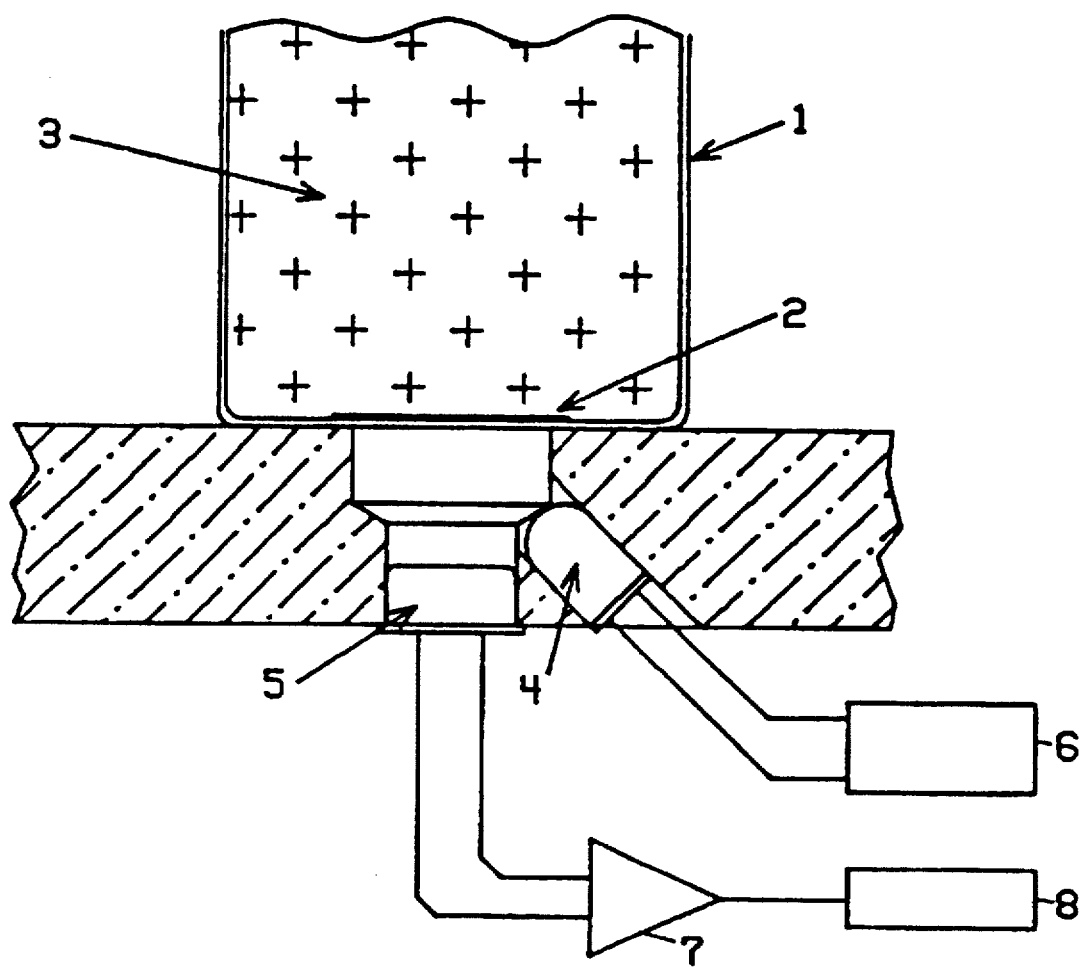
FIG. 1—Blood culture instrument
Figure 2:
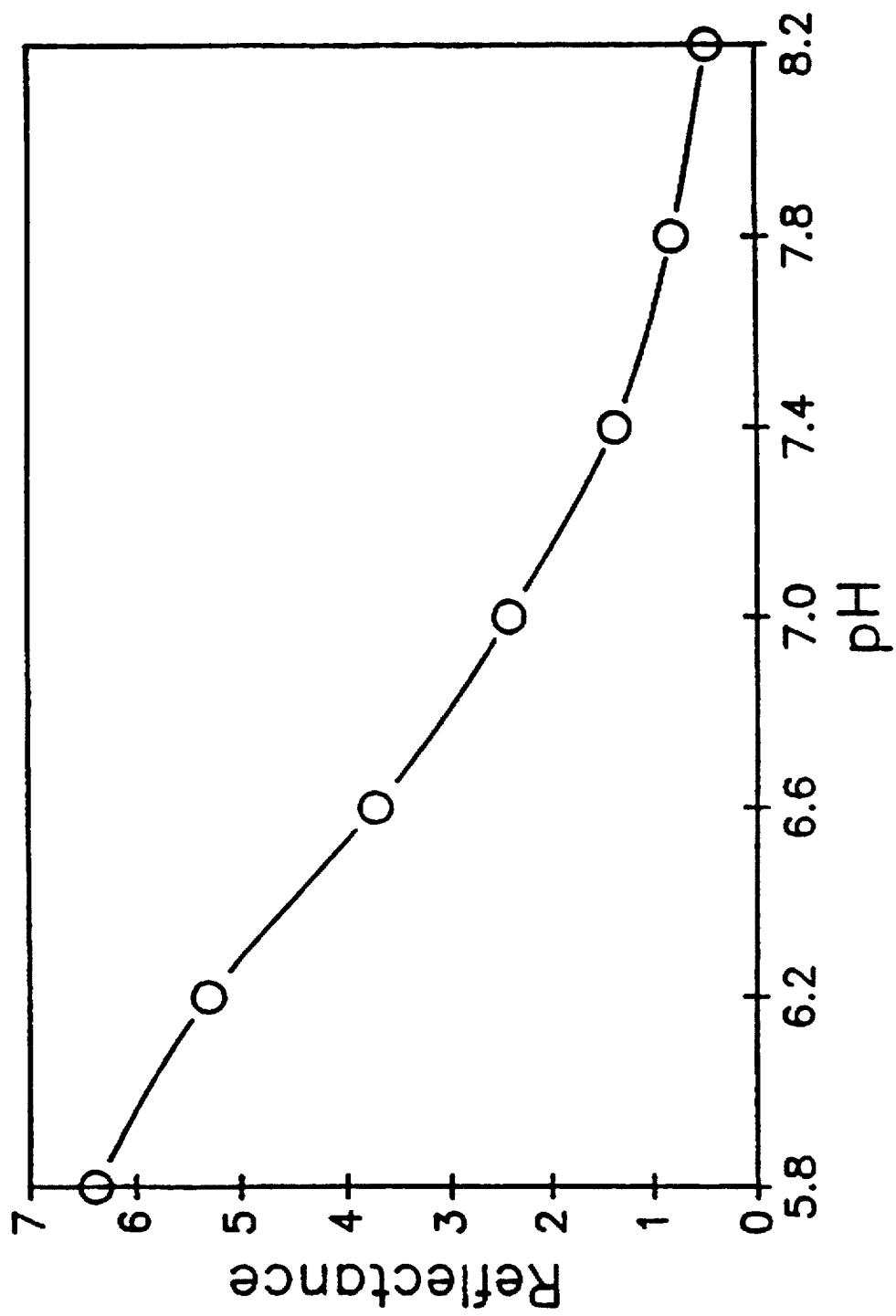

FIG. 2—pH Sensitivity

Besides testing the instrument subjectively with various colored bottles, it was tested with the pH sensitive membrane bottles. This figure shows the average voltage output of seven different detectors after equilibration of the sensor with various buffers over a pH range of 5.8 to 8.2. Detailed studies showed that the system could reliably distinguish changes of 0.1 pH unit over a range of pH 6.0 to 7.5.

Figure 3:
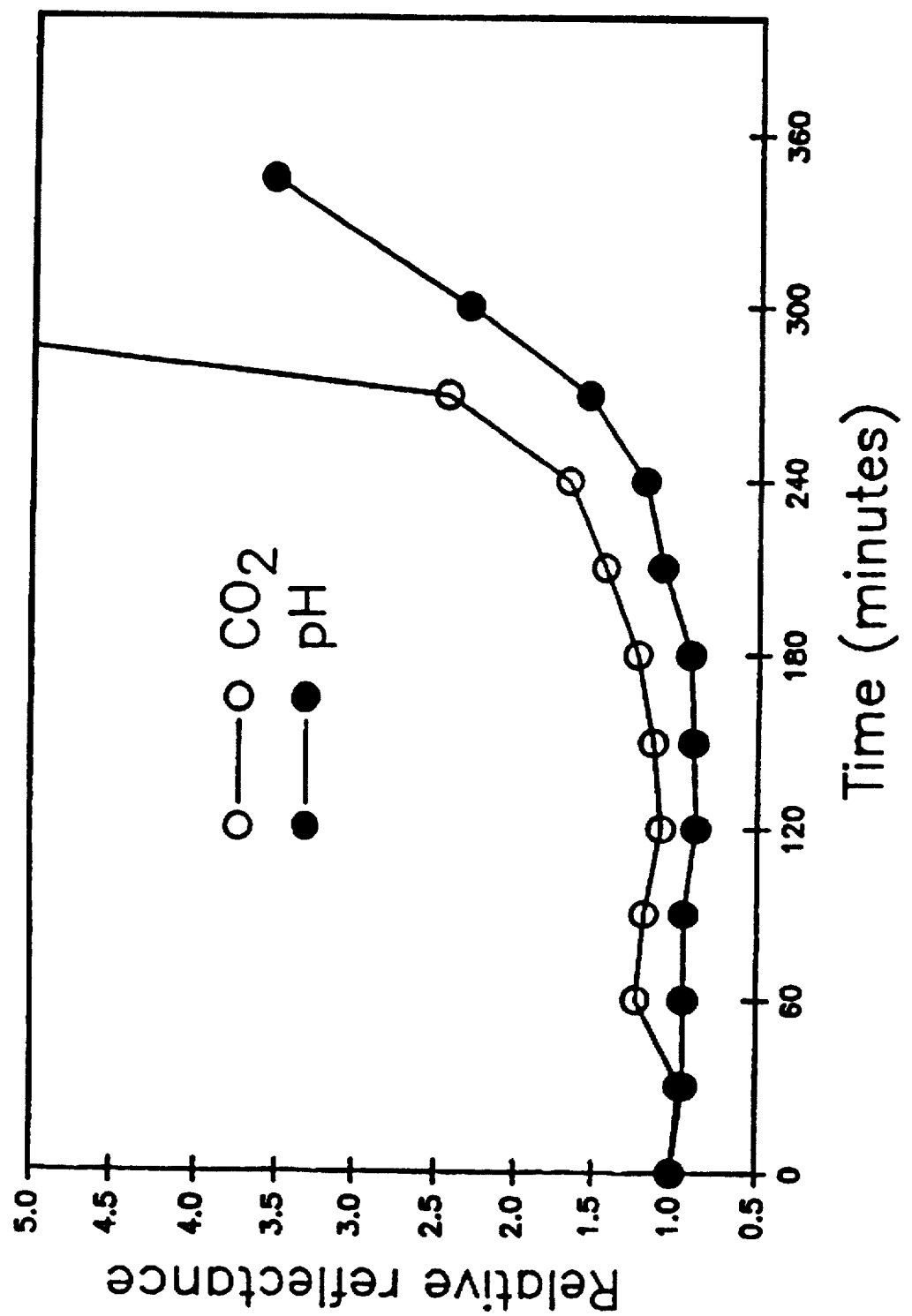

FIG. 3—pH and atmosphere change with microbial growth

The instrument was used to detect microbial growth by both pH change and by gas or volatile production. This figure shows the change in pH and in $CO_2$ resulting from growth of the bacterium, *E. coli*.

Figure 4:
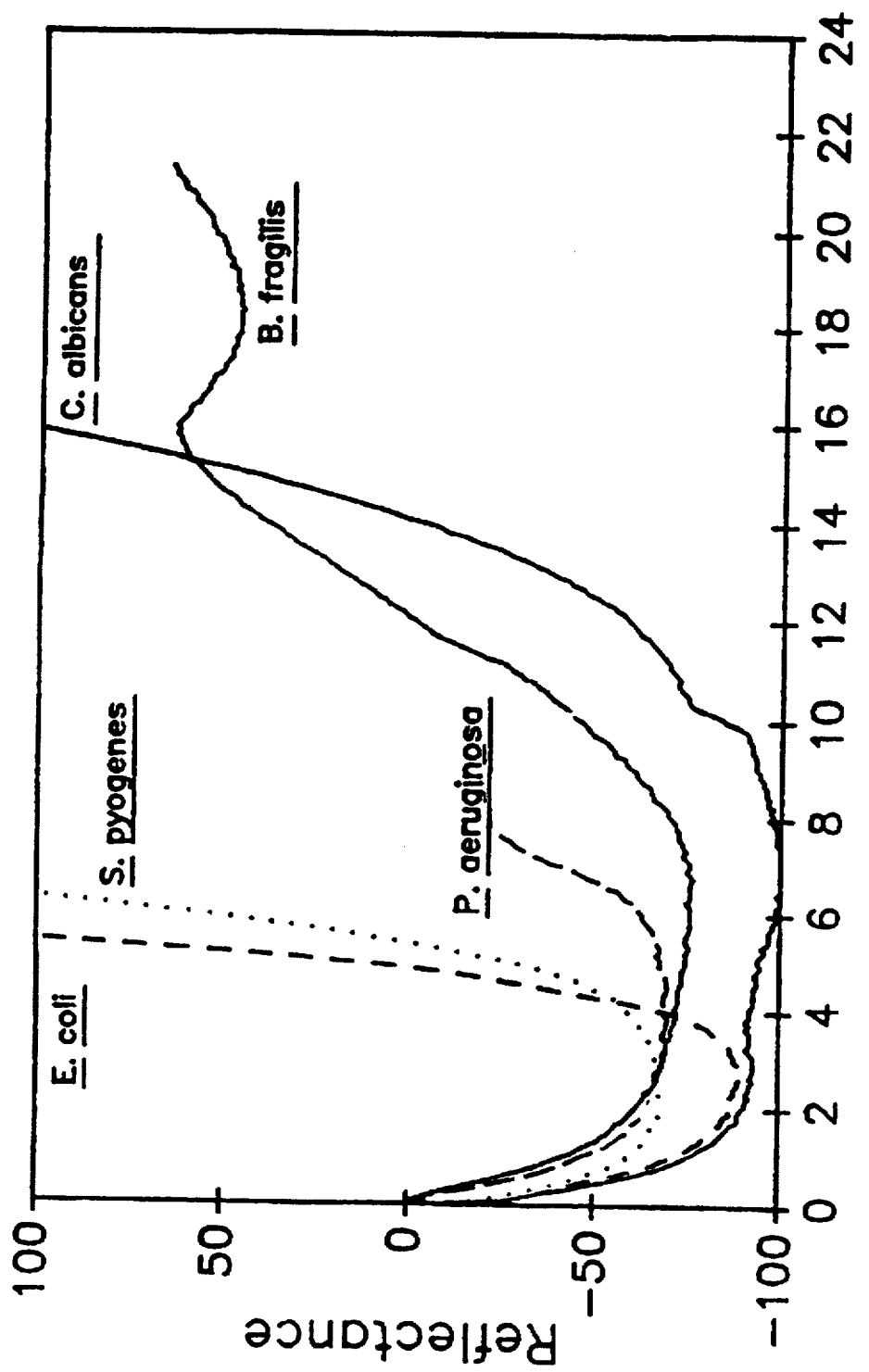

FIG. 4—Detection of a variety of microorganisms

Essentially all organisms will release gases or volatile acids in the course of their metabolism. Thus, this system can be used to detect the growth of a very wide range of microorganisms. This figure shows the detection of gases ($CO_2$) and/or volatile acids produced during the growth of *E. coli*, a Gram negative bacterium; *S. pyogenes*, a Gram positive bacterium; *P. aeruginosa*, a Gram negative non-fermenting bacterium; *B. fragilis*, an anaerobic bacterium; and *C. albicans*, a yeast. The units indicate relative gas concentration in the medium based on $CO_2$ concentration at the beginning of the assay. Because the sample containers and media are at room temperature (approximately 20° C.), and the container and sample are incubated at 37° C. during the assay, $CO_2$ is released into the space above the liquid sample and medium during the first 2 to 4 hours because of the reduced solubility of $CO_2$ in the liquid as temperature increases. Unless the containers and media are maintained at the higher temperature before introduction of the sample and placement into the instrument, reliable indication of the presence of microorganisms cannot be measured until after the minimum $CO_2$ concentration is passed, typically within the first 2 to 4 hours.

FIGS. 5A–5D

FIGS. 5A–5D illustrate one embodiment of the permeable membrane, where the permeable membrane is disposed within a cavity in a stopper of the bottle having the sensor therein.

FIG. 6

Figure 6:
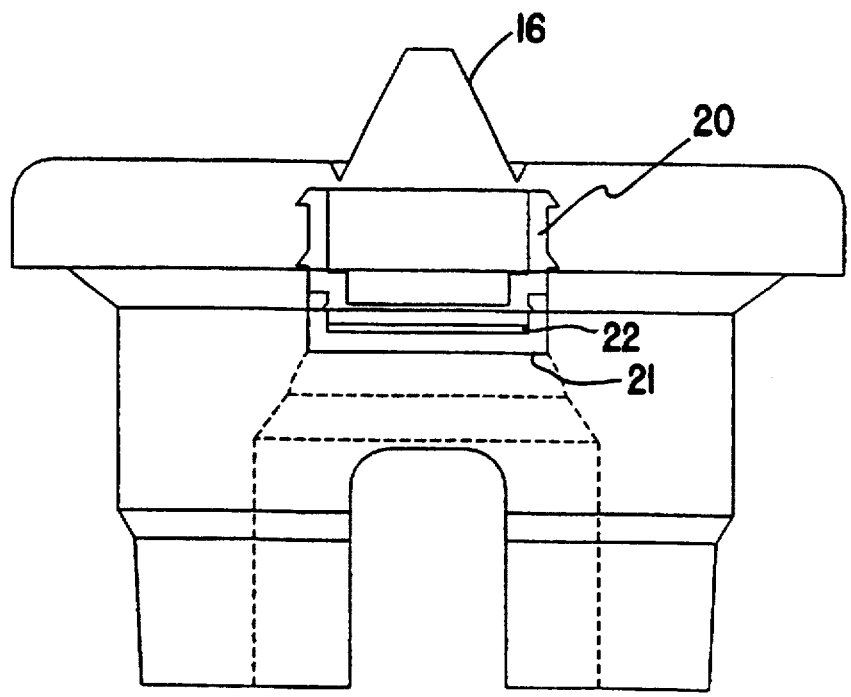

FIG. 6 is a cross-sectional view of a stopper having a particular permeable membrane and support grid.

Figure 7A:
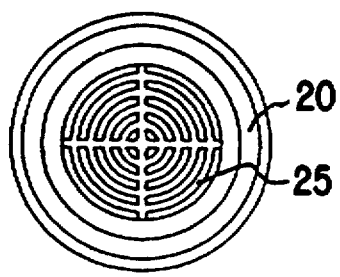
Figure 7B:
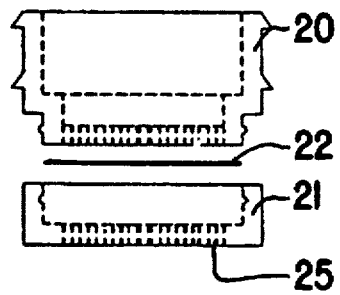

FIGS. 7A and 7B

FIG. 7A is a top view of one of the support grids for the permeable membrane, and FIG. 7B is an exploded view the membrane supports.

FIGS. 8A–8C

Figure 8A:
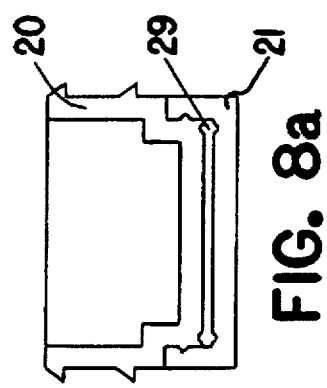
Figure 8B:
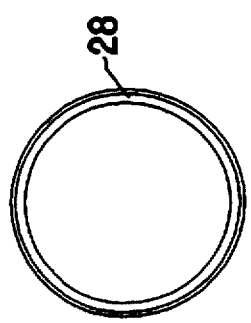
Figure 8C:
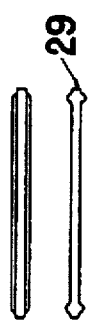

FIGS. 8A–8C are views of membrane support grids for holding a membrane molded with an O-ring.

FIG. 9

Figure 9:
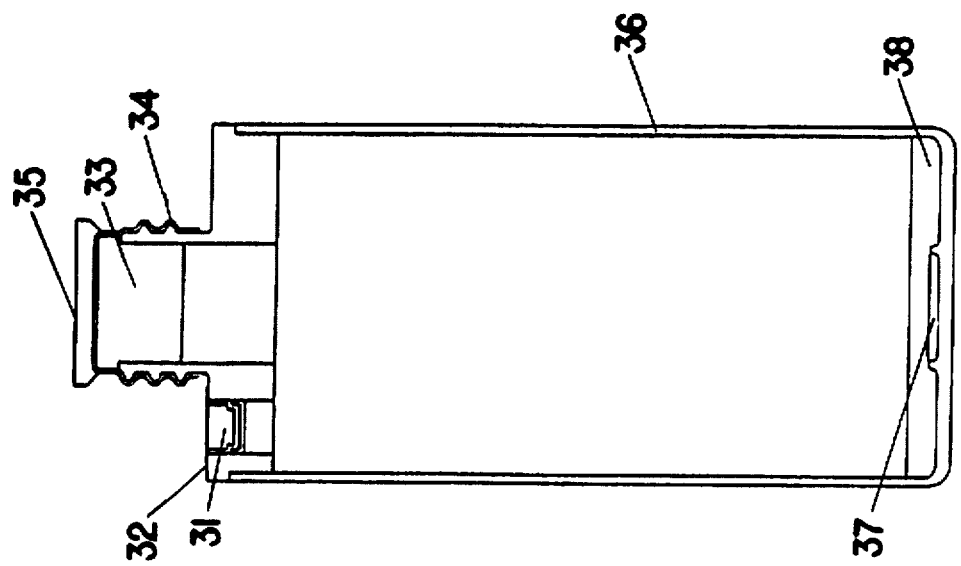

FIG. 9 is a cross-sectional view of the culture bottle of the present invention having the sensor and permeable membrane therein.

Figure 10B:
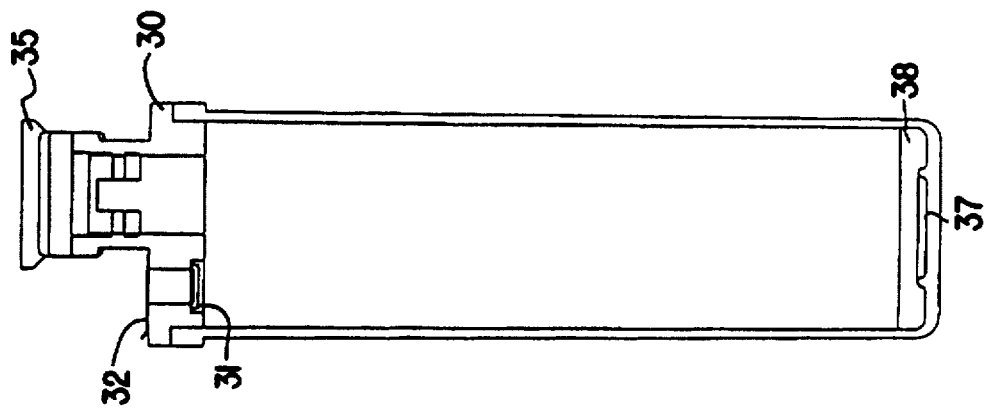
Figure 10A:
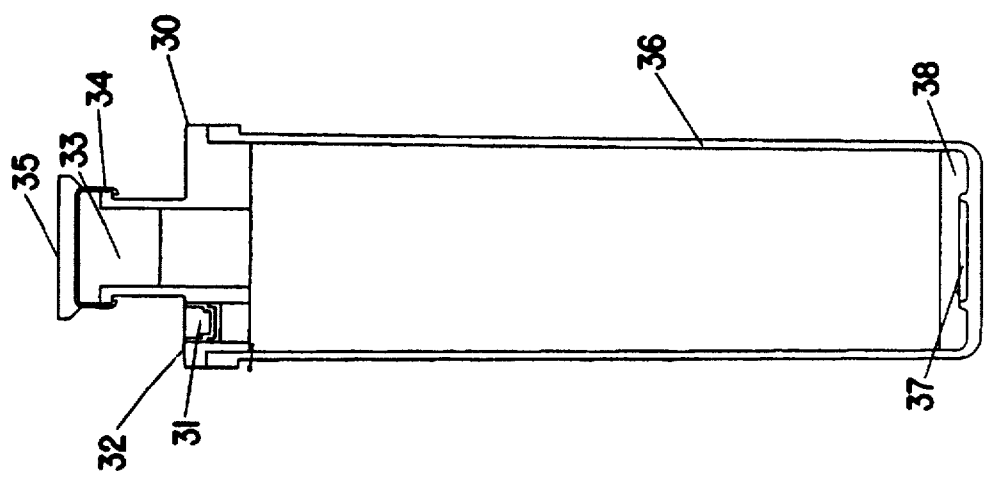

FIGS. 10A and 10B

FIG. 10A illustrates the culture bottle with the bottle opening in the center of the bottle cap, and in FIG. 10B, the bottle access opening is off-center.

FIG. 11

Figure 11:
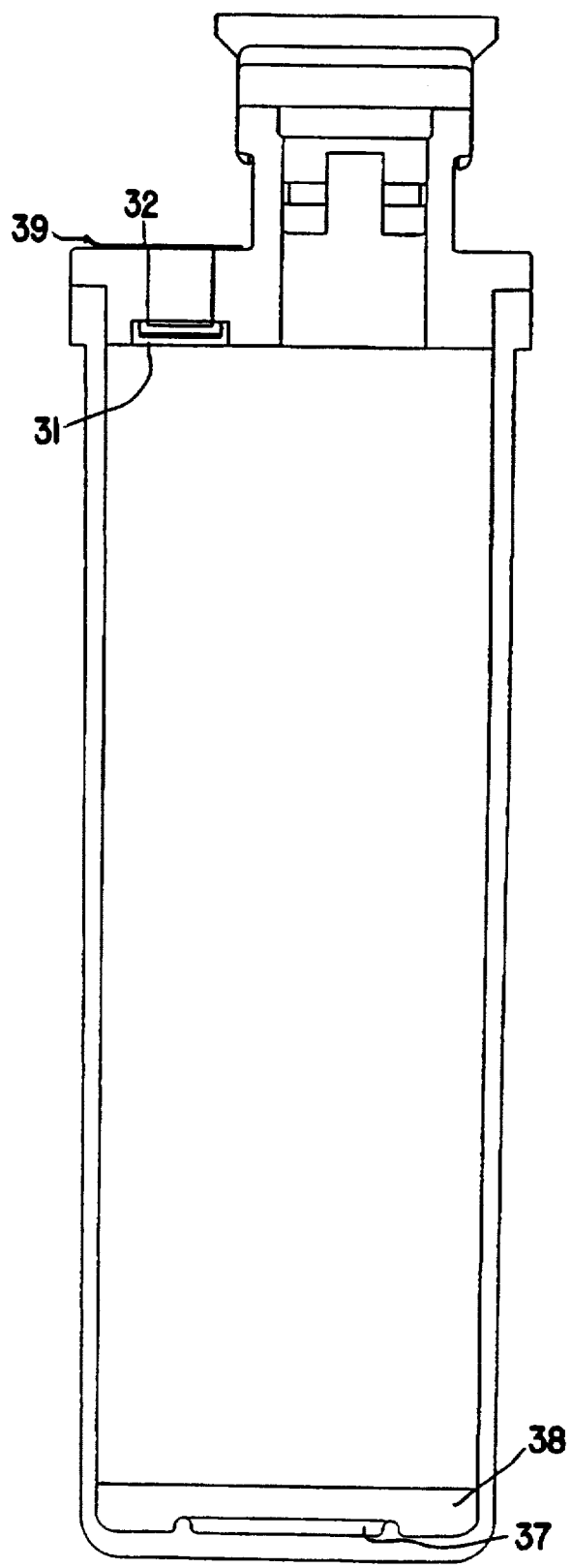

FIG. 11 illustrates the culture bottle of the present invention having the sensor therein, as well as the gas permeable membrane and an impermeable removable seal.

FIGS. 12A–12C

Figure 12B:
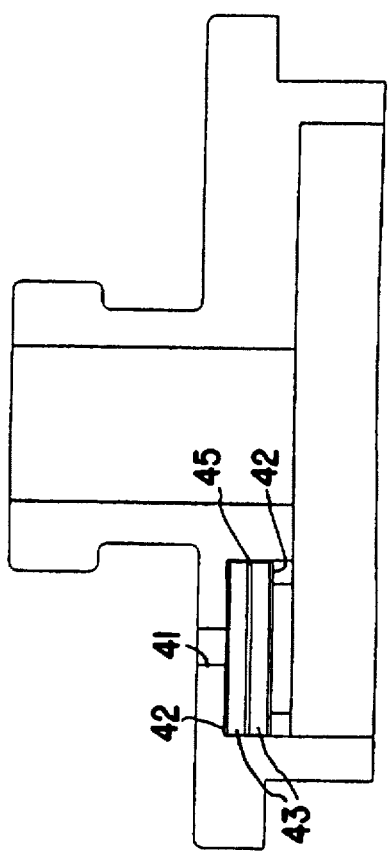
Figure 12C:
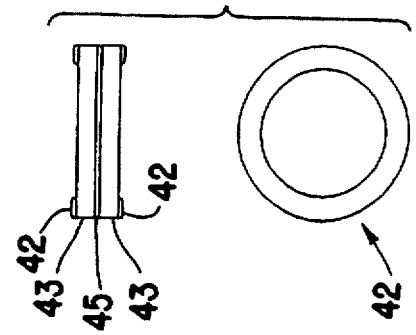
Figure 12A:
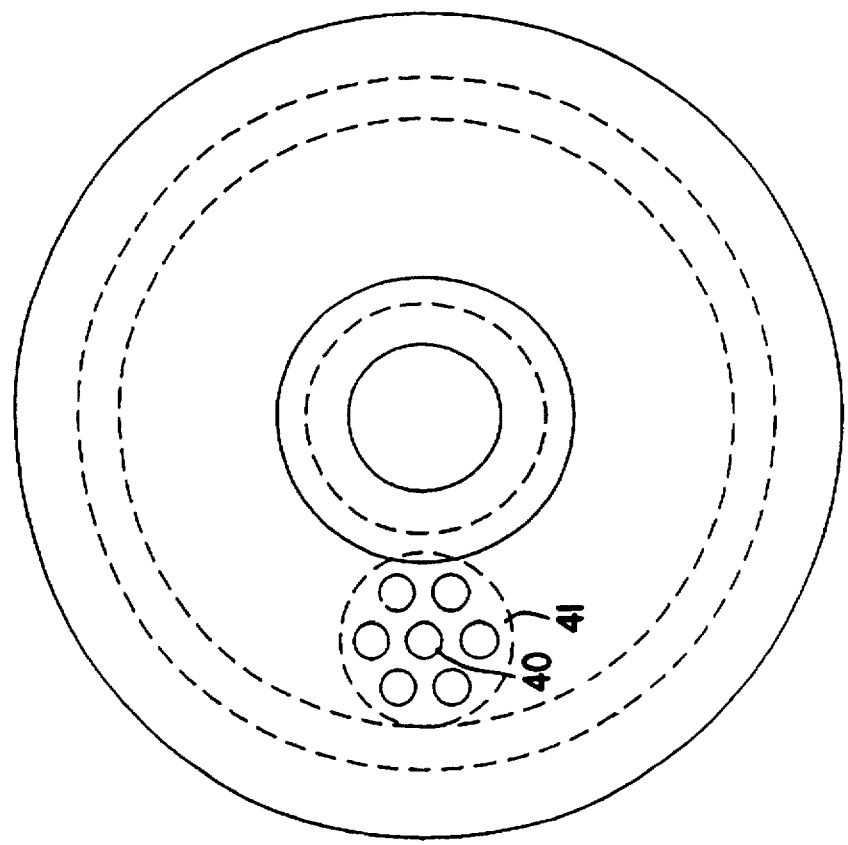

FIGS. 12A–12C illustrate an additional embodiment of the gas permeable membrane within the cap of the culture bottle.

Figure 13A:
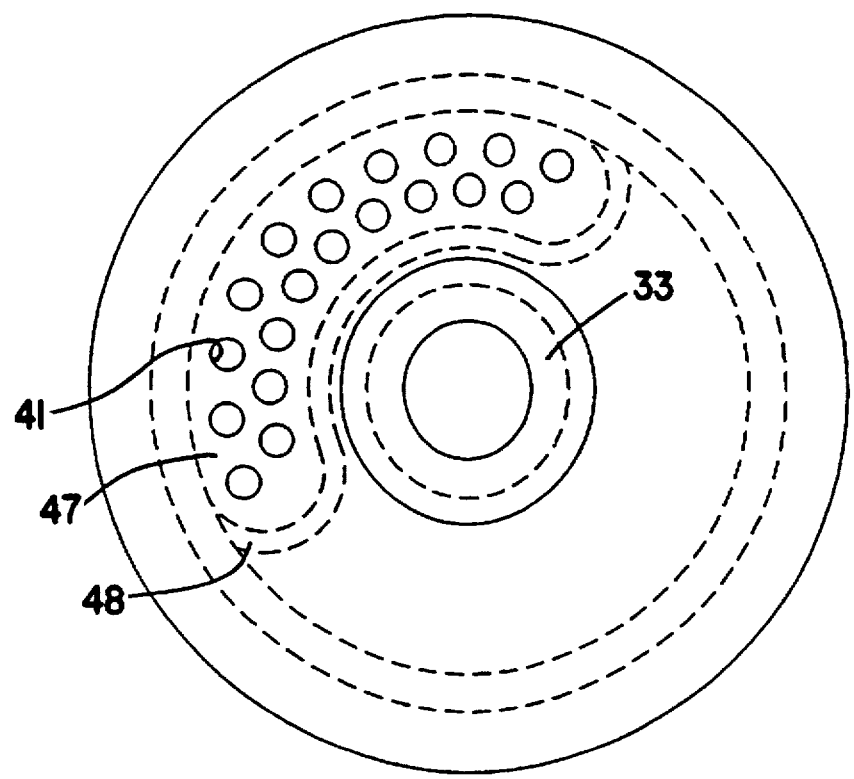
Figure 13B:
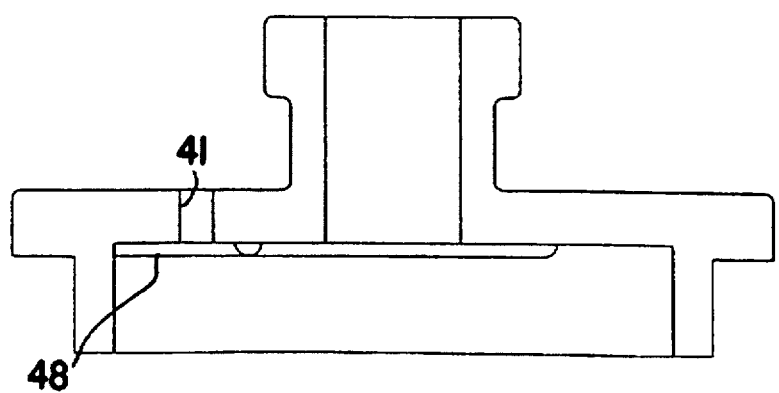

FIGS. 13A and 13B

FIGS. 13A and 13B illustrate an embodiment of the invention where the grid and permeable membrane are C-shaped.

FIG. 14

Figure 14:
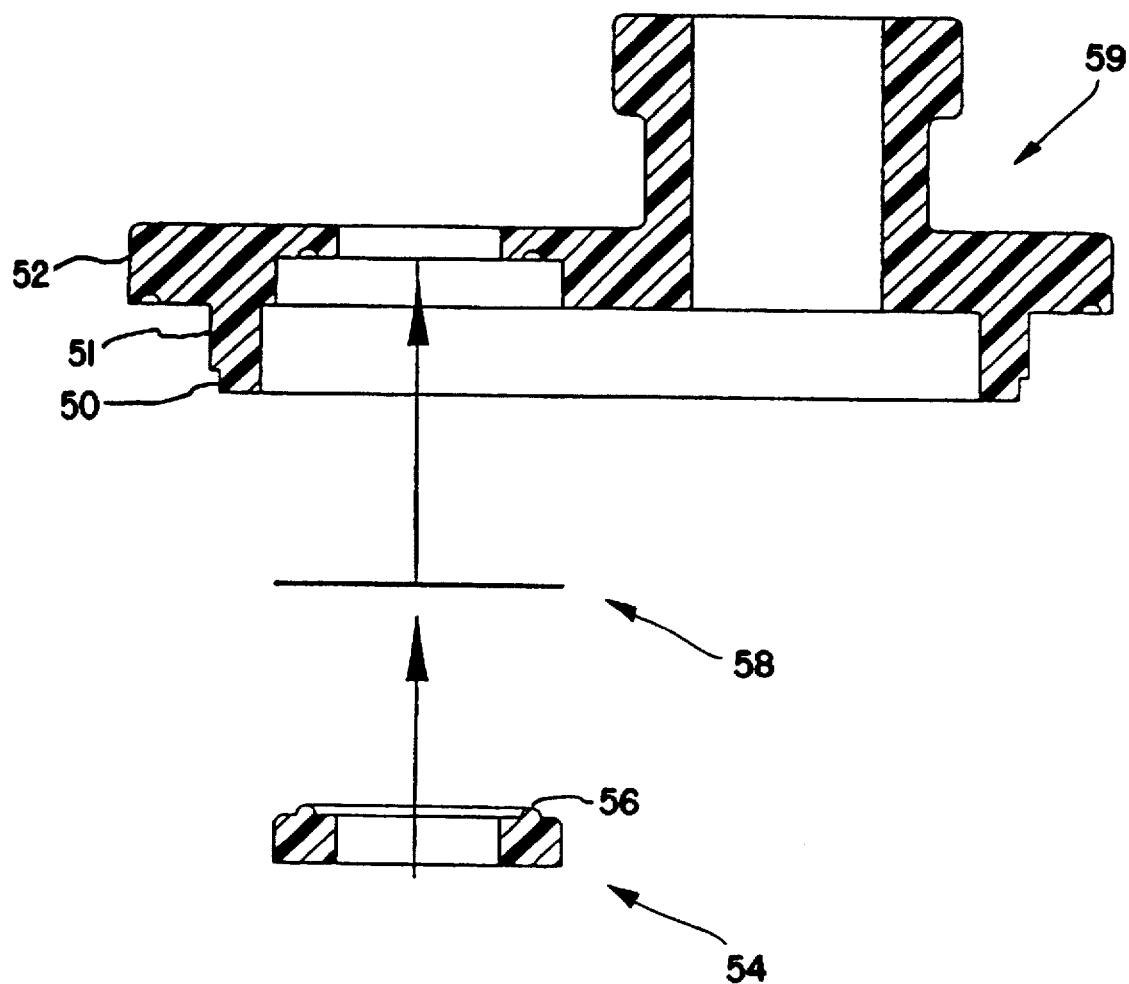

FIG. 14 is a cross-sectional view of particular features of the culture bottle cap and retaining ring for the permeable membrane.

Figure 15A:
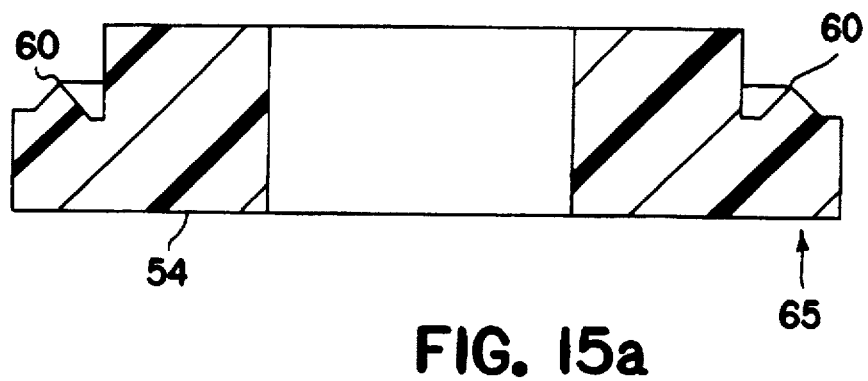
Figure 15B:
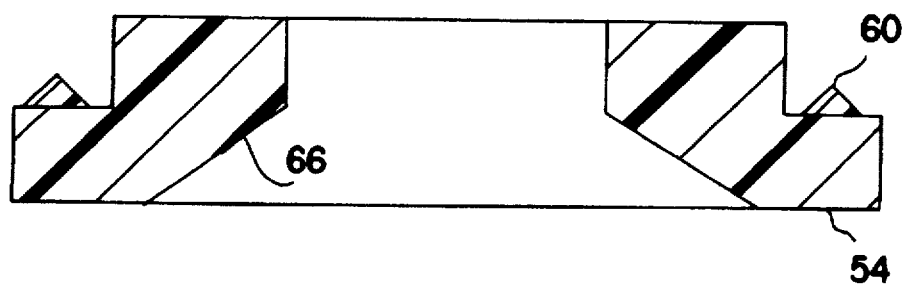

FIGS. 15A and 15B

FIGS. 15A and 15B are cross-sectional illustrations of additional embodiments of the retaining ring for the permeable membrane.

FIG. 16

Figure 16:
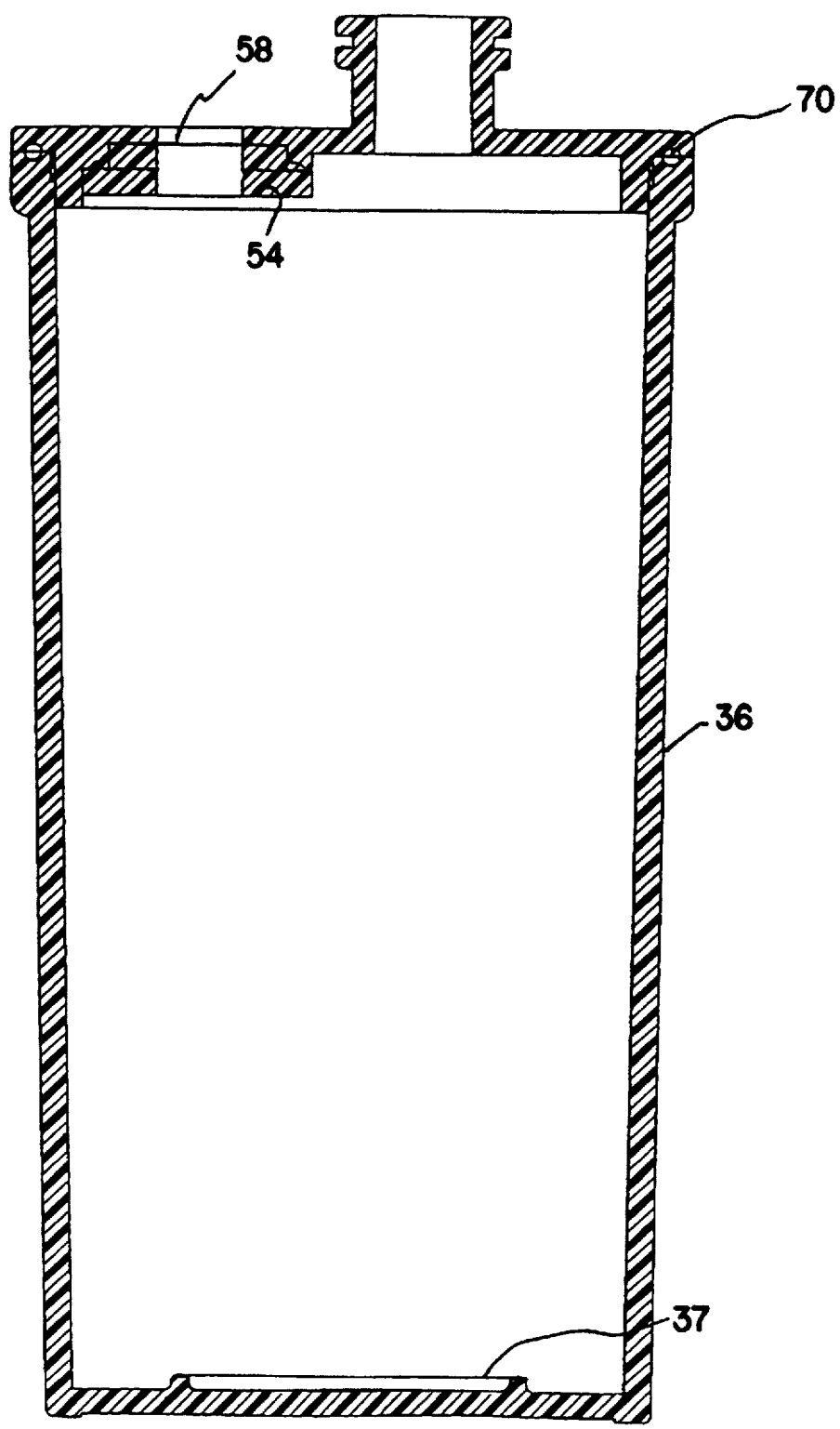

FIG. 16 is an illustration of the overall culture bottle.

DESCRIPTION OF PREFERRED EMBODIMENTS

The apparatus and device of the invention provide a non-invasive means for detecting the presence of microorganisms in clinical specimens, such as blood samples or other body fluids, and in non-clinical specimens by measuring an increase in metabolic products produced by microorganisms. The specimen is added to a specially formulated medium that enhances the production of certain microbial metabolic products, which are detected by a unique disposable sensor located at the bottom of a culture container or in the sealing means of the container. The sensor comprises a solid composition or membrane, which is referred to as an attachment or support medium, with an indicator medium immobilized on or within it. The sensor is located flush against the inside surface of a container, in the sealing means used to seal the container or attached to the sealing means, such that the indicator medium is visible from outside. It may be affixed to the container to prevent cells, proteins, other solids or other opaque or colored components from getting between it and the container surface. In certain embodiments the sensor is separated from the specimen and its growth medium by a membrane or solid layer that permits the passage of gas molecules but prevents passage of ions.

One embodiment of this invention comprises a sealing means, such as a cap or lid, which may be transparent or which may have a transparent section. The sensor can be placed in proximity to the transparent cap or section of cap or is made part of the cap. When the cap is used to seal the container, the changes in indicator are read through the transparent sealing means. An advantage seen to this embodiment is that this may be the most economical way to produce the containers on a large scale.

The sealing means may also be made of a material, such as a polymer, which contains encapsulated indicator micelles. A transparent section in either the container or the sealing means is not needed, as long as the material is permeable to the metabolic products of the microorganisms and the changes in the indicator are visible on the surface of the sealing means.

Microorganisms in specimens of body fluids, such as blood, containing as few as 1 organism per milliliter, can be detected using this invention. Such specimens may require up to 7 days incubation before the population of organisms reaches a critical level and where an increase in metabolic products can be measured. We found a concentration of $10^6$ CFU/ml for certain types of organisms provided measurable changes in pH or $CO_2$. All organisms showed measurable results at concentrations of $10^7$ to $10^8$ CFU/ml.

The sensor is useful in that: 1) the microbial metabolic products are measured in the liquid phase of the culture bottle rather than in the atmosphere over the specimen, 2) because the unique disposable sensor is affixed to the interior surface of the bottle or the closure or sealing means or attached through the outside of the closure or sealing means, measurements can be made from outside the transparent wall of the bottle or the sealing means without having to violate the integrity of the bottle, 3) the external measurements can be made by visual inspection or with an instrument that measures by reflectance, 4) opaque or colored components in the specimen do not interfere with the ability of the sensor to detect changes or the measurement of those changes, and 5) a high concentration of indicator molecules is maintained within a small volume in the sensor, i.e., within the polymer emulsion or on the membrane, such that a color change can be easily observed.

The nutritional components that make up a complex microbial medium influence the metabolic pathways used by microorganisms. Organic acids, bases and various gases are produced in proportions dependent on the nutrients available. These products also vary from species to species of microorganism. The presence of these products in the liquid medium can change its pH. The sensors used in the invention contain pH sensitive indicators that give a measurable change in response to a pH change in the environment. In the embodiment in which the pH sensor is covered by a gas-permeable, ion-impermeable membrane, the presence of gases that affect the pH of the indicator, such as $CO_2$, is measured. Thus, microbial growth can be detected either by changes in pH of the liquid culture medium or by measurement of gases dissolved in the medium, both indications are caused by metabolic gaseous products produced by microorganisms. Carbon dioxide is a common metabolite produced by most organisms and, therefore, is the preferred metabolite for detection of microbial growth.

$CO_2$ and pH sensors share two common components, a molecular species useful as a pH indicator and an attachment/support medium. The pH indicator can be attached either covalently or non-covalently to the support medium. Alternately, the indicator can be encapsulated within a polymer matrix such as being emulsified within a polymer matrix prior to curing. To perform as a pH sensor, indicator must be in contact with the liquid medium. The $CO_2$ sensor has a third component, a semi-permeable substance that completely separates the indicator membrane from the specimen and growth medium. The semi-permeable layer may be a separate membrane, alternatively, the cured polymer adjacent to the specimen and growth medium may form an integral semi-permeable membrane. These sensors are affixed inside a suitable transparent vessel or a transparent sealing means with an appropriate adhesive. They may also comprise an integral part of the sealing means or be affixed to the sealing means or within the vessel as an indicator emulsified within a polymer matrix cured in situ. They can also be placed outside the container, as long as a method is provided that allows the metabolic products of the microorganisms or the growth medium containing the specimen to contact the sensor.

A variety of different fluorescent and visible pH indicators can be used as the active molecular species in pH or $CO_2$ sensors. Generally, the only limitations on the selection of indicators are the requirements that they have acceptable dynamic pH ranges and wavelength changes that are readily detectable by existing front surface fluorescence or reflectance technologies.

Sensors for detecting pH changes in the culture medium according to the invention preferably exhibit a change in fluorescence intensity or visible color over a pH range of about 5.0 to about 8.0.

Indicators for the $CO_2$ sensor should exhibit a change in fluorescence intensity or visible color preferably between about pH 13 and about 5, and most preferably between about pH 13 to about 9, in order to detect changes in $CO_2$ concentration.

Only certain pH indicator molecules can be bound covalently or non-covalently to a support medium and retain their pH indicating properties. Indicators belonging to the xanthene, phenolphthalein and phenolsulfonphthalein groups are useful. Examples of these include fluorescein, coumarin, phenolphthalein, thymolphthalein, bromothymol blue, thymol blue, xylenol blue and α-naphthol benzein.

The attachment/support medium can be a substance such as cellulose, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with the microbial growth medium.

The pH indicator sensors directly detect pH changes due to the pH environment of the microbial growth medium. However, these sensors can be made to selectively react to gases (e.g., carbon dioxide, ammonia) in the liquid growth medium by covering them with a selectively semi-permeable composition or membrane, such as silicone, latex, teflon, or various plastics characterized by the capacity to selectively permit the diffusion of a gas while preventing the passage of ions. For sensors comprising indicator encapsulated within a polymer matrix, the polymer forming the matrix can act as the semi-permeable barrier that permits the passage of gases but not ions.

In one embodiment, the $CO_2$ sensor is comprised of four components. The first component is a visual or fluorescent pH indicator, which is reactive at the pH range between 6 and 10. Examples of indicators meeting these criteria are bromothymol blue, thymol blue, xylenol blue, phenolphthalein, coumarin, and fluorescein. The second component is sodium hydroxide or an equivalent base, which maintains an optimal pH environment for detection of $CO_2$ by the selected pH indicator. The third component is glycerol or an equivalent emulsifier, which can produce droplets of indicator solution emulsified within the uncured polymer. The fourth component is the uncured polymer such as silicone, which maintains a proper environment for the indicator. Any polymer can be used that does not affect the chemical activity of the indicator, either from its own chemical or physical properties or its requirements for curing, as long as it is permeable to gases but not ions, and does not have these properties altered when subjected to sterilization. Other silicone polymers that are also satisfactory are those that are cured by high temperature, by catalytic activity, or by ultraviolet vulcanization. An emulsion is prepared from the four components and the polymer is cured to form a semipermeable matrix around the droplets of pH indicator, which permits selective diffusion of $Co_2$ and other gases from the liquid microbial growth medium, resulting in a measurable change in the indicator. The sensor can be prepared separately, such as in a mold, cured, and then attached to the culture bottle with an appropriate adhesive, such as a silicone adhesive. Alternatively, and preferably, the sensor is formed on the bottom of the bottle and cured in situ. After curing the bottle with the sensor is sterilized, such as by autoclaving. Conveniently, the growth medium can be introduced into the bottle before autoclaving and also sterilized by that process.

The culturing of aerobic microorganisms requires a supply of oxygen within the culture bottle. Currently, automated, semi-automated and some manual culture bottles are transiently vented in some manner, for example by insertion and removal of a venting device (a venting spike or needle, for example), loosening and/or exchange of a cap, or mechanical withdrawal of gas from and forced gas return to the bottle. Some non-agitating manual systems employ an indwelling venting device that remains in place for the duration of testing.

However, in the present invention, a selective hydrophobic barrier is provided in the bottle which allows passage of ambient atmosphere into the culture bottle while preventing leakage of media and specimen out of the bottle. The permeable barrier of the present invention preferably prevents contaminants, such as contaminating organisms, from entering the bottle, as well as discourages the passage of carbon dioxide out of the bottle. Preferred materials for the permeable membrane/hydrophobic barrier, include silicone, polypropylene, fluorinated ethylene propylene, low density polyethylene, Porex, polytetrafluoroethylene and polymethylpentene membranes and materials as selective barriers (polymethylpentene having negligible $CO_2$ permeability and high $O_2$ permeability—270(cc-m)/sec-cm$^2$-cmHg×10$^{-10}$). Other permeable membranes are also feasible if sufficiently permeable to oxygen, preferably if the membrane discourages the passage of carbon dioxide out of the bottle, and if the material is autoclavable and resistant to leaking under pressure. As will be discussed below, materials lacking sufficient rigidity, can be reinforced by forming a support structure integral with the permeable membrane, or by placing the permeable membrane on or between support means.

Adhesives can be utilized in some embodiments of the present invention for securing the permeable membrane to a support material. Adhesives such as Elmers Stix-All can be used to seal Porex plugs securely within a stopper. Adcare adhesive, though not sufficient for providing a hermetic seal, is permeable to gas and can be used to adhere a membrane to a Porex plug in a sandwich-like configuration.

In order to prevent oxygen passage into the culture bottle prior to use of the bottle for culturing, a hermetic seal is provided for covering the gas permeable membrane. The impermeable seal covers and hermetically seals the permeable membrane during bottle preparation, gassing, autoclaving and storage. The seal is removed at the time of bottle inoculation (if the microorganism is aerobic) to allow exchange of gasses during incubation of the media bottle. Though it may depend upon what material the permeable membrane is disposed within, plastic coated aluminums are generally suitable.

Further with respect to the gas permeable membrane, a pore size of 0.2 microns or less is desirable for preventing contamination of the media by ambient organisms during the transfer of gas across the membrane. A support system for securing the gas permeable membrane in place is needed, and the same or a separate support structure should support the gas permeable membrane if necessary, against interior pressure and vacuum effects due to autoclaving. PTFE with an internal polypropylene support grid, is particularly beneficial for use as the gas permeable membrane.

Figure 5A:
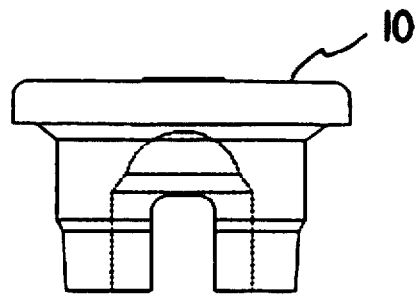
Figure 5B:
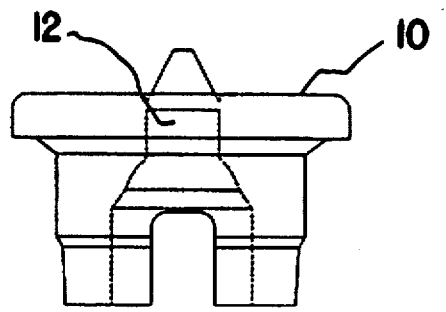
Figure 5C:
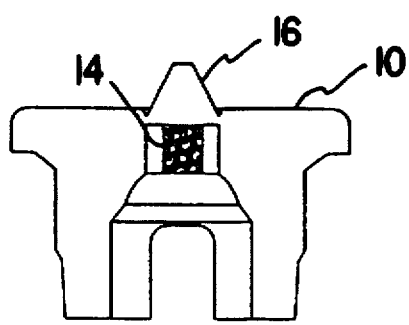
Figure 5D:
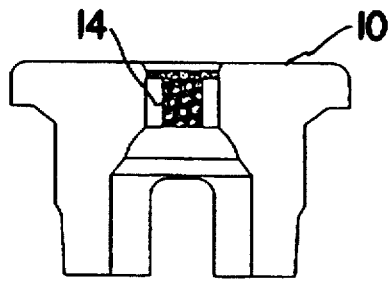

One embodiment of the invention is illustrated in FIGS. 5A to 5D. A stopper 10 such as illustrated in FIG. 5A, is provided with an internal cavity 12 as illustrated in FIG. 5B. A filter 14 is disposed within the cavity of the stopper, with a gas impermeable removable seal 16 disposed adjacent filter 14 (see FIG. 5C). As shown in FIG. 5D, when the removable impermeable seal 16 is removed, the stopper 10 is permeable to gas via gas permeable membrane 14. Gas permeable membrane 14 can be, for example, a Porex filter.

As illustrated in FIG. 6, in a different embodiment of the stopper of the present invention, a gas impermeable seal 16 is provided above two supports 20, 21 having a gas permeable membrane 22 therebetween. As can be better seen in FIGS. 7A and 7B, a support grid 25 is provided in both upper support 20 and lower support 21. When the two supports 20, 21 are snapped together, the gas permeable membrane 22 is securely held therebetween. In another embodiment of the supports for the gas permeable membrane, as can be seen in FIGS. 8A to 8C, a membrane 28 held between supports 20 and 21, can be molded with an "O-ring" seal 29 so as to improve the impermeability of the membrane to the passage of liquids out of the culture bottle. Of course, the supports and membrane therebetween, are provided in a stopper, which is likewise provided in a culture bottle having the sensor of the present invention.

In another embodiment of the present invention, the gas permeable membrane is not provided in the stopper, but rather adjacent the stopper in an upper portion of the culture bottle. As can be seen in FIG. 9, a gas permeable membrane 31 is provided below a gas impermeable removable seal, such as a foil seal 32. A stopper 23 is provided such as a 20 mm stopper, as well as a metal seal 34 and a flip top 35. Bottle 36 can be a plastic bottle with sensor 37 and membrane 38 disposed at the bottom thereof, as discussed previously. As can be seen in FIG. 10A, the stopper 33, which can be a 12 mm stopper, is disposed in a center position of plastic cap 30 on bottle 36. Also, as can be seen in FIG. 10B, the stopper can be provided off-center on the cap.

As illustrated in FIG. 11, above membrane 31 is disposed a foil seal 32. Seal 32 can be a plastic coated aluminum, of course other materials for the removable seal are contemplated as long as such materials have sufficient impermeability and ease of removability from the bottle at the time of culturing. As can be seen in FIG. 11, a tab 39 not adhered to the bottle, is provided as part of seal 32, for ease of grasping and removing the seal.

In a further embodiment of the present invention as illustrated in FIGS. 12A to 12C, a grid 40 is formed within the bottle cap itself. In one embodiment, a plurality of holes 41 are formed through the bottle cap. As can be seen in FIGS. 12B and 12C, layers 43 of Porex can be disposed adjacent the gas permeable membrane 45 and held in place by retaining rings 42. This assembly, as seen in FIG. 12B, is disposed beneath grid 40 of the bottle cap.

The grid can be such as grid 47 illustrated in FIGS. 13A and 13B, where the plurality of holes 41 are in a C-shape around the central stopper 33. In this way, the surface area of the gas permeable membrane 48 disposed below the grid, can be increased.

The culture bottle of the present invention can be manufactured in a number of ways. In a preferred embodiment, the culture bottle and the culture bottle cap are manufactured separately, and then subsequently adhered together, such as by gluing the top onto the bottle. Another method of adhering the bottle top and bottle is by spin welding, where the bottle top and bottom are rotated relative to each other such that the generated friction melts the plastic, which resolidifies with the top and bottle thus welded together.

As can be seen in FIG. 14, bottle cap 59 is provided with external surfaces 50, 51 and 52, each having a different external diameter. Surface 52 is of a dimension so as to be flush with the outer circumferential surface of the bottle. Surface 50, the surface with the smallest external diameter, fits exactly within the bottle, such that the internal diameter of the bottle and the external diameter defined by surface 50, are essentially the same. Surface 51 has an external diameter greater than the internal diameter of the bottle. As such, during spin welding, surface 51 having a greater diameter than the internal diameter of the bottle, creates a high degree of friction as the bottle cap is spun and pressed into the bottle. In this way, the bottle top and bottle are firmly adhered to each other. As also shown in FIG. 14, membrane 58 is held in place by retaining ring 54 having a projection 56 for improved impermeability to fluid flow around the retaining ring and membrane.

Another method of adhering the bottle cap to the bottle is by ultrasonic welding. The retaining ring for holding the gas permeable membrane in place, can also be adhered by ultrasonic welding. As can be seen in FIGS. 15A and 15B, the retaining ring 54 illustrated in cross-section, is provided with an annular peak 60. When ultrasonic energy is applied at point 65 directly below peak 60, the retaining ring 54 can be welded in place. As can be seen in FIG. 15B, a sloped internal surface 66 can be provided to decrease the likelihood of liquid being trapped in the retaining ring during shaking of the bottle.

As illustrated in FIG. 16, a sensor 37 is disposed in the bottom of the culture bottle, with membrane 58 held in place by retaining ring 54. Also illustrated is an annular recess 70 for excess melted plastic generated during spin welding of the cap to the bottle due to the melting of surface 51 (see FIG. 14). Due to annular recess 70, melted plastic does not flow to exterior surfaces of the bottle cap or bottle.

Due to the responsiveness of the sensor in one embodiment of the present invention, to carbon dioxide or pH, it is desirable if the gas permeable membrane is more permeable to oxygen (entering the bottle) than to carbon dioxide (exiting the bottle). A membrane at least partially impermeable to carbon dioxide will allow for a higher sensitivity of the sensor. However, a membrane more permeable to oxygen than carbon dioxide is not necessary for the present invention. Though it was initially believed that a culture bottle would not be workable that allows for a free flow of carbon dioxide out of the bottle as well as requires carbon dioxide within the bottle for altering the sensor therein (so as to indicate the presence of, for example, a microorganism). Surprisingly, it was discovered that the sensor acts as some type "sink" for the carbon dioxide in the bottle such that the sensor will properly indicate the presence of a microorganism even with the gas permeable membrane as part of the bottle.

Permeability by Blood Gas Change (Table 1)

Bottles were prepared and gassed with 100% nitrogen. Representative bottles were unsealed by removing the heat seal and allowed to shake on a rotary shaker at room temperature for 1 hour. At the end of the time period, $pO_2$ was measured on a blood gas instrument and readings compared to a control bottle without a permeable membrane and to a predetermined $pO_2$ of 20–30 mm Hg (found in previous testing to represent bottles gassed with 100% nitrogen). An increase in the $pO_2$ of these bottles as compared to the control and reference value indicated permeability of the material to oxygen within 1 hour.

Autoclavability (Table 1)

Selected test materials were autoclaved at 121° C., 15 psi for 12 minutes on fast exhaust. The materials were then examined for visible changes such as melting or deformation.

Pressure Tolerance (Table 1)

Stoppers were prepared with test materials as described without a heat seal then crimp sealed onto bottles containing water. A 60 cc syringe was fitted with a 16 g needle, the plunger pulled back to the 50 cc mark, and the needle inserted into the stopper. Pressure was then applied to the plunger until leakage occurred through the material. When leakage occurred, the amount of pressure required was determined by subtracting the plunger position from 50.

TABLE 1

PHYSICAL TESTING OF MEMBRANES

| Test Material | Auto-clavable? | Pressure Tolerance | pO₂ at 1 hour | Interpretation |
|---|---|---|---|---|
| No membrane, hole in stopper, sealed | | | 81.4 mm Hg | Negative Control |
| No membrane, hole in stopper, unsealed | | | 167.7 mm Hg | Negative Control |
| Porex X4709 | Yes | <5 psi | 155.4 mm Hg | Unacceptable |
| PTFE adhered to X4709 | Yes | 17–20 psi | 117.8 mm Hg | Acceptable |
| 0.005 mil AeroRubber | Yes | 17–20 psi | 37.7 mm Hg | Unacceptable |

Permeability by Growth Performance (Table 2)

Representative bottles were incoculated. Bottles were prepared as described above. Representative bottles were then inoculated with *C. albicans*, *P. aeruginosa* and *M. luteus*, 2 bottles per test material using standard growth performance protocols. Negative control bottles were prepared with an atmosphere of 5% carbon dioxide in nitrogen. These bottles were not transiently vented and did not have a permeable membrane. Positive control bottles were prepared in the same manner but vented or were standard aerobic adult bottles. Inoculated bottles were left in the BTA for 3 days and readings were then graphed. By comparison of the graphs, it was determined that *M. luteus* was the best indicator of oxygen passage into the bottles at a rate that did not inhibit growth. Also, since this was a low carbon dioxide producing organism, the effect of carbon dioxide diffusion could be observed.

TABLE 2

PERMEABILITY OF MEMBRANES BY GROWTH PERFORMANCE OF *M luteus*

| Test Material | Total Readings Change | Time to Detection |
|---|---|---|
| Standard Aerobic Adult Bottle, Vented | 1057 RU | 31.5 hrs. |
| Standard Aerobic Adult Bottle, Not Vented | 161 RU | No Growth |
| Unvented Bottle with 5% Carbon Dioxide in Nitrogen | 230 RU | No Growth |
| 0.005 mil AeroRubber Membrane | 166 RU | No Growth |
| PTFE Membrane | 535 RU | 31.0 hrs. |

Heat Seal Permeability (Table 3)

Using a hollow punch, holes were cut into standard Tompkins stoppers. Test heat seal materials were sealed over the hole. Bottles were filled with 40 ml of media, overlaid with heat-sealed stoppers, gassed with 100% nitrogen and autoclaved for 12 minutes at 121° C., 15 psi. After equilibration for a minimum of 24 hours, pO₂ of representative bottles was measured on the NOVA STAT 3 using standard protocols. Remaining bottles were held at room temperature for a period of time to determine if the heat seals allowed leakage of oxygen into the bottle. Comparison of the pO₂ initially vs. control bottles without a cored stopper vs. end pO₂ after the holding time determined if the material was permeable to oxygen.

TABLE 3

HEAT SEAL PERMEABILITY TESTING

| Test Material | Autoclavable? | Initial pO₂ | pO₂ after 2 weeks at Room Temperature | Interpretation |
|---|---|---|---|---|
| Zip Lock A-Line Pouch | Yes | 29.0 | 25.7 | Acceptable |
| Mylar Pouch | No | | | Not Acceptable |
| MPFL, Wraps, Inc. | Yes | 29.2 | 26.9 | Acceptable |
| PPFL, Wraps, Inc. | No | | | Not Acceptable |

Though a number of methods could be used for making the culture bottle of the present invention, in one method the gas permeable membrane material is attached to the cap of the bottle by heat sealing. A removable seal is then attached over the permeable material, outside of the bottle. The cap is welded into place on the bottle. In a separate port, the sensor is added and heat cured. Subsequently, media is added to the bottle, and the headspace of the bottle is evacuated and replaced with an appropriate gas mixture. A residual vacuum can then be applied. A stopper is secured in place with a seal, after which the assembled bottle is autoclaved.

During autoclaving, pressure inside the bottle can exceed 15 psi. As such, as in one embodiment of the present invention, the gas permeable membrane structure, as well as the gas impermeable removable seal are constructed so as to withstand pressures of from 5 to over 30 psi. Preferably, the permeable membrane structure and removable seal are capable of withstanding pressures of at least 15 psi. And, because pressure from organism growth can reach up to 25 psi, the gas permeable membrane structure and the removable seal are each constructed so as to be capable of withstanding pressures of from 15 to 25 psi, and in one preferred embodiment, the membrane and seal are constructed so as to withstand pressures of 25 psi or more. After autoclaving, the bottles are allowed to cool, and can then be labeled for packaging and shipping.

In one method for using the bottle, a blood sample is taken from a patient such as by using a butterfly needle with tubing secured to a vacutainer adapter. The top of a stoppered port is decontaminated and the adapter is slipped over the port. Then, the bottle will draw the appropriate amount of sample. Once inoculated, the bottle is identified and ready for culturing. If the bottle is to be used for aerobic culture, the removable seal is peeled off, exposing the gas permeable membrane and thus allowing for the free passage of oxygen into the bottle. The bottle can be placed into an automated culturing instrument such as the BacT/Alert instrument by Organon Teknika. The bottle is incubated at a temperature of 35°–37° C.

In a number of culturing methods, it is desirable to shake the culture bottle during culturing. The culture bottle of the present invention is particularly suitable for being shaken during culturing as the gas permeable membrane allows for a free flow of oxygen into the culture bottle but at the same time restricts fluid flow out of the bottle. In fact, it has been found that the present invention is particularly suitable for vigorous shaking, as well as shaking the culture between upright and inverted positions. A spiked bottle from the prior art would leak and thus could not be shaken or rocked in this way.

The principles, preferred embodiments, and modes of operation of the invention have been described in the foregoing specification. The invention which is intended to be protected herein, however, is not to be constrained as limited to the particular forms disclosed, since these are to be regarded as illustrative rather than restrictive. Variations and changes may be made by those skilled in the art without departing from the spirit and scope of the invention. For example, both the sensor and permeable membrane can be provided in other parts of the culture bottle, other than disclosed. For example, the permeable membrane could be disposed in a side wall of the bottle, or the sensor could be disposed within the cap of the bottle. Also, a plurality of sensors or membranes might be provided. Furthermore, other arrangements for support grids and sizes and shapes of permeable membranes, would also be within the scope of the invention. And, of course, other materials for the permeable membrane and impermeable removable seal, would also be within the scope of this invention.

We claim:

1. A device for detecting microorganisms comprising:

a container for holding a sample to be analyzed for the presence or absence of micro organisms;

growth medium within said container for supporting growth of microorganisms;

a sensor within said container separate from said growth medium, said sensor being responsive to changes in concentration of a gas component within said container, the gas component concentration changing due to growth of microorganisms, so that said sensor is capable of indicating the presence or absence of microorganisms within the sample; and a gas permeable membrane in a wall of said container for allowing passage of gas during use of the device.

2. The device of claim 1, wherein said gas component is a metabolic product of microorganisms in the sample.

3. The device of claim 2, wherein said sensor is responsive to changes in pH due to said gas metabolic products of microorganisms in the sample.

4. The device of claim 2, wherein the metabolic product is carbon dioxide, and said sensor is responsive to increases in carbon dioxide.

5. The device of claim 1, wherein said sensor is affixed to an interior surface of a portion of the container, and wherein said container portion is substantially transparent.

6. The device of claim 1, wherein said gas permeable membrane is a hydrophobic barrier for containing the sample within the container.

7. The device of claim 6, wherein said gas permeable membrane is constructed so as to withstand pressures of from 5 to about 30 psi.

8. The device of claim 7, wherein a reinforcing means is provided within or proximate to the gas permeable membrane for providing support to the gas permeable membrane when under pressure.

9. The device of claim 8, wherein said gas permeable membrane is comprised of polytetrafluoroethylene and said reinforcing means is a polypropylene support grid within said gas permeable membrane.

10. The device of claim 8, further comprising an O-ring disposed adjacent the circumference of the gas permeable membrane.

11. The device of claim 6, wherein said gas permeable membrane is constructed so as to withstand pressures of 15 psi or more.

12. The device of claim 11, wherein said gas permeable membrane is constructed so as to withstand pressures of 25 psi or more.

13. The device of claim 6, further comprising a hermetic gas impermeable removable seal covering said gas permeable membrane.

14. The device of claim 13, wherein said removable seal is comprised of a plastic coated aluminum.

15. The device of claim 13, wherein said gas permeable membrane has a pore size of 0.2 microns or less.

16. The device of claim 13, wherein a reinforcing means is provided within or proximate to the gas permeable membrane for providing support to the gas permeable membrane when under pressure.

17. The device of claim 16, wherein said reinforcing means comprises two support grids disposed on either side of the gas permeable membrane.

18. The device of claim 16, wherein said container is a bottle and said gas permeable membrane and impermeable seal are disposed within a bottle cap for fitting with the bottle, and said reinforcing means comprises a plurality of apertures in the bottle cap adjacent to where said gas permeable membrane is disposed within the bottle cap.

19. The device of claim 18, wherein said gas permeable membrane and the arrangement of apertures in the bottle cap are C-shaped.

20. The device of claim 18, wherein said sensor is disposed within the bottle cap.

21. The device of claim 18, wherein said sensor is disposed within a bottom portion of the bottle.

22. The device of claim 13, wherein said container is a bottle and said gas permeable membrane and impermeable seal are disposed within a bottle cap for fitting with the bottle.

23. The device of claim 1, wherein said gas permeable membrane is formed of one or more materials selected from silicone, polypropylene, acrylic copolymers, fluorinated ethylene propylene, low density polyethylene, polytetrafluoroethylene and polymethylpentene.

24. The device of claim 1, wherein said gas permeable membrane is more permeable to oxygen than to carbon dioxide.

25. The device of claim 24, wherein said gas permeable membrane is comprised of polymethylpentene.

26. The device of claim 1, further comprising fluid media for aiding microorganism growth within the device.

27. The device of claim 26, further comprising a removable gas impermeable seal disposed adjacent said gas permeable membrane.

28. The device of claim 27, further comprising an inert gas within said container.

29. The device of claim 28, wherein said gas is nitrogen and/or $CO_2$.

* * * * *

UNITED STATES PATENT AND TRADEMARK OFFICE
CERTIFICATE OF CORRECTION

PATENT NO. : 5,795,773
DATED : August 18, 1998
INVENTOR(S) : Read et al.

It is certified that error appears in the above-identified patent and that said Letters Patent is hereby corrected as shown below:

Claim 1, line 3, delete "micro organaisms" and replace with -- microorganisms --.

Signed and Sealed this

Seventeenth Day of November, 1998

Attest:

BRUCE LEHMAN

Attesting Officer

Commissioner of Patents and Trademarks